United States Patent
Gat

(10) Patent No.: US 7,805,178 B1
(45) Date of Patent: Sep. 28, 2010

(54) DEVICE, SYSTEM AND METHOD OF RECEIVING AND RECORDING AND DISPLAYING IN-VIVO DATA WITH USER ENTERED DATA

(75) Inventor: Daniel Gat, Haifa (IL)

(73) Assignee: Given Imaging Ltd., Yoqneam (IL)

(*) Notice: Subject to any disclaimer, the term of this patent is extended or adjusted under 35 U.S.C. 154(b) by 77 days.

(21) Appl. No.: 11/492,218

(22) Filed: Jul. 25, 2006

Related U.S. Application Data

(60) Provisional application No. 60/701,986, filed on Jul. 25, 2005.

(51) Int. Cl.
*A61B 5/05* (2006.01)

(52) U.S. Cl. ............. 600/407; 600/424; 345/619

(58) Field of Classification Search .......... 345/619; 600/424, 407
See application file for complete search history.

(56) References Cited

U.S. PATENT DOCUMENTS

| | | |
|---|---|---|
| 3,683,389 A | 8/1972 | Hollis |
| 3,971,362 A | 7/1976 | Pope et al. |
| 3,984,628 A | 10/1976 | Sharp |
| 4,273,431 A | 6/1981 | Farmer et al. |
| 4,278,077 A | 7/1981 | Mizumoto |
| 4,416,283 A | 11/1983 | Slocum |
| 4,532,918 A | 8/1985 | Wheeler |
| 4,539,603 A | 9/1985 | Takeuchi et al. |
| 4,646,724 A | 3/1987 | Sato et al. |
| 4,689,621 A | 8/1987 | Kleinberg |
| 4,741,327 A | 5/1988 | Yabe |
| 4,786,982 A | 11/1988 | Wakahara et al. |
| 4,841,291 A | 6/1989 | Swix et al. |
| 4,844,076 A | 7/1989 | Lesho et al. |
| 5,010,412 A | 4/1991 | Garriss |

(Continued)

FOREIGN PATENT DOCUMENTS

DE 34 40 177 11/1984

(Continued)

OTHER PUBLICATIONS

U.S. Appl. No. 10/200,548, filed Jul. 23, 2002, Glukhovsky et al.

(Continued)

*Primary Examiner*—Brian Casler
*Assistant Examiner*—James Kish
(74) *Attorney, Agent, or Firm*—Pearl Cohen Zedek Latzer, LLP

(57) ABSTRACT

The present invention discloses a system comprising an in vivo imaging device able to transmit in vivo data via a wireless medium, a receiver to receive in vivo data via the wireless medium, input means for entering to the receiver indications by a user, an indication storage unit to store the indications and to store data representing entering time at which the indications was entered by the user and information identifying in vivo data portions corresponding to that entering time, and a display unit to display the indications concurrently with the in vivo data portions corresponding to the entering time at which the indications was entered. The indications entered by the user may be indicative of activities of the user, condition of the user, environmental conditions next to the user and the like.

4 Claims, 4 Drawing Sheets

U.S. PATENT DOCUMENTS

| | | |
|---|---|---|
| 5,187,572 A | 2/1993 | Nakamura et al. |
| 5,202,961 A | 4/1993 | Mills et al. |
| 5,267,033 A | 11/1993 | Hoshino |
| 5,279,607 A | 1/1994 | Schentag et al. |
| 5,351,161 A | 9/1994 | MacKay et al. |
| 5,355,450 A | 10/1994 | Garmon et al. |
| 5,486,861 A | 1/1996 | Miyamoto et al. |
| 5,495,114 A | 2/1996 | Adair |
| 5,519,828 A | 5/1996 | Rayner |
| 5,604,531 A | 2/1997 | Iddan et al. |
| 5,643,175 A | 7/1997 | Adair |
| 5,678,568 A | 10/1997 | Uchikubo et al. |
| 5,749,367 A | 5/1998 | Gamlyn et al. |
| 5,761,655 A * | 6/1998 | Hoffman .................. 707/4 |
| 5,819,736 A | 10/1998 | Avny et al. |
| 5,833,603 A | 11/1998 | Kovacs et al. |
| 5,875,280 A | 2/1999 | Takaiwa et al. |
| 5,886,353 A | 3/1999 | Spivey et al. |
| 5,909,026 A | 6/1999 | Zhou et al. |
| 5,929,901 A | 7/1999 | Adair et al. |
| 5,986,693 A | 11/1999 | Adair et al. |
| 5,993,378 A | 11/1999 | Lemelson |
| 6,043,839 A | 3/2000 | Adair et al. |
| 6,077,223 A | 6/2000 | Satherley |
| 6,108,571 A | 8/2000 | Minoz et al. |
| 6,240,312 B1 | 5/2001 | Alfano et al. |
| 6,310,642 B1 | 10/2001 | Adair et al. |
| 6,328,212 B1 | 12/2001 | Metlitasky et al. |
| 6,351,606 B1 | 2/2002 | Yamazaki |
| 6,594,036 B1 | 7/2003 | Wong et al. |
| 6,607,301 B1 | 8/2003 | Glukhovsky et al. |
| 6,636,263 B2 | 10/2003 | Oda |
| 6,667,765 B1 | 12/2003 | Tanaka |
| 6,689,056 B1 | 2/2004 | Kilcoyne et al. |
| 6,690,412 B1 | 2/2004 | Higo |
| 6,709,387 B1 | 3/2004 | Glukhovsky et al. |
| 6,865,718 B2 | 3/2005 | Montalcini |
| 7,009,634 B2 | 3/2006 | Iddan et al. |
| 7,039,453 B2 | 5/2006 | Mullick et al. |
| 2001/0019364 A1 | 9/2001 | Kawahara |
| 2001/0035902 A1 | 11/2001 | Iddan et al. |
| 2002/0042562 A1 | 4/2002 | Meron et al. |
| 2002/0093484 A1 | 7/2002 | Skala et al. |
| 2002/0103417 A1 | 8/2002 | Gazdzinski |
| 2002/0171669 A1* | 11/2002 | Meron et al. .................. 345/619 |
| 2003/0013951 A1 | 1/2003 | Stefanescu et al. |
| 2003/0028078 A1 | 2/2003 | Glukhovsky |
| 2003/0117491 A1 | 6/2003 | Avni et al. |
| 2003/0144711 A1* | 7/2003 | Pless et al. .................. 607/60 |
| 2003/0174208 A1 | 9/2003 | Glukhovsky et al. |
| 2005/0075551 A1 | 4/2005 | Horn et al. |
| 2005/0207645 A1 | 9/2005 | Nishimura et al. |
| 2006/0158512 A1 | 7/2006 | Iddan et al. |
| 2007/0106750 A1* | 5/2007 | Moore .................. 709/217 |

FOREIGN PATENT DOCUMENTS

| | | |
|---|---|---|
| EP | 0 667 115 | 8/1995 |
| EP | 0 677 272 | 10/1995 |
| EP | 0 941 691 | 9/1999 |
| EP | 0 977 278 | 2/2000 |
| EP | 1 779 777 | 5/2007 |
| JP | 5745833 | 3/1982 |
| JP | 3289779 | 12/1991 |
| JP | 4022325 | 1/1992 |
| JP | 4109927 | 4/1992 |
| JP | 1992-144533 | 5/1992 |
| JP | 4180736 | 6/1992 |
| JP | 5015515 | 1/1993 |
| JP | 05-200015 | 8/1993 |
| JP | 6285044 | 10/1994 |
| JP | 08-248326 | 9/1996 |
| JP | 09-327447 | 12/1997 |
| JP | 11225996 | 8/1999 |
| JP | 3017770 | 12/1999 |
| JP | 2001-025004 | 1/2001 |
| JP | 2001-224553 | 8/2001 |
| KR | 99-68036 | 8/1999 |
| WO | WO 92/21307 | 12/1992 |
| WO | WO 97/33513 | 9/1997 |
| WO | WO 98/11816 | 3/1998 |
| WO | WO 99/21359 | 4/1999 |
| WO | WO 00/22975 | 4/2000 |
| WO | WO 00/76391 | 12/2000 |
| WO | WO 01/08548 | 2/2001 |
| WO | WO 01/35813 | 5/2001 |
| WO | WO 01/50941 | 7/2001 |
| WO | WO 01-65995 | 9/2001 |
| WO | WO 01-87377 | 11/2001 |
| WO | WO 02/080376 | 10/2002 |
| WO | WO 02/094337 | 11/2002 |
| WO | WO 02/095351 | 11/2002 |
| WO | WO 03/003706 | 1/2003 |
| WO | WO 03-009739 | 2/2003 |
| WO | WO 03/011103 | 2/2003 |
| WO | WO 03/028224 | 4/2003 |
| WO | WO 2004-082472 | 9/2004 |

OTHER PUBLICATIONS

U.S. Appl. No. 10/724,109, filed Dec. 1, 2003, Glukhovsky et al.
U.S. Appl. No. 11/094,831, filed Mar. 31, 2005, Bettesh et al.
U.S. Appl. No. 11/337,570, filed Jan. 24, 2006, Iddan et al.
U.S. Appl. No. 11/295,491, filed Dec. 7, 2005, Iddan et al.
U.S. Appl. No. 11/363,185, filed Feb. 28, 2006, Iddan et al.
"A Low-Power Miniature Transmitter Using a Low-Loss Silicon Platform for Biotelemetry" Ziaie B et al 19 Annual International Conference of The IEEE Engineering in Medicine and Biology Society. vol. 5, 1994 pp. 2221-2224.
BBC News Online—Pill Camera to "Broadcast from the Gut", Feb. 21, 2000, www.news.bbc.co.uk.
Australian Office Action, Application No. 2005-244523 dated Feb. 6, 2007.
European Search Report Application No. 07001478 completed Apr. 2, 2007.
European Search Report Application No. 07001479 dated Apr. 10, 2007.
"Integrated RF Transmitter Based on SAW Oscillator" Heuberger A et al. 23$^{rd}$ European Southampton, UK Sep. 16-18, 1997, Piscataway, NJ USA IEEE, pp. 344-347.
International Search Report—PCT application No. PCT/IL01/00218, dated May 7, 2002.
Japanese Office Action, Application No. 2005-156061 dated Nov. 2, 2005.
Japanese Office Action, Application No. 2005-156060 mailed Aug. 29, 2005.
Japanese Office Action, Application No. 2001-564653 dated Jun. 12, 2007.
Korean Office Action, Application No. 2006-7019809 dated May 28, 2007.
Manual of Photogrammetry, Thompson (Ed.), Third Edition, vol. Two, American Society of Photogrammetry, 1966.
Office Action U.S. Appl. No. 09/800,470 dated Sep. 27, 2004.
Office Action U.S. Appl. No. 09/800,470 dated Aug. 4, 2005.
Supplementary European Search Report Application No. 01912088 dated Mar. 21, 2006.
Supplementary European Search Report Application No. 06010954.3 dated Aug. 3, 2006.
Supplementary European Search Report Application No. 06010954.3 dated Nov. 7, 2006.
The Radio Pill, Rowlands, et al. British Communications and Electronics, Aug. 1960, pp. 598-601.
Video Camera to "Take"—RF System Lab.

Wellesley Company Sends Body Monitors into Space—Crum, Apr. 1998.

Wireless Transmission of a Color Television Moving Image from the Stomach Using a Miniature CCD Camera, Light Source and Microwave Transmitter. Swain CP, Gong F, Mills TN. Gastrointest Endosc 1997; 45:AB40.

www.jason.net—Tiny cam © 2000.

www.pedinc.com—Personal Electronic Devices, Inc. © 1997.

International Search Report WO 2004/82472, Application No. PCT/IL04/00265, International Filing Date: Mar. 23, 2004.

Office Action U.S. Appl. No. 10/004,270 mailed Jun. 3, 2004.

Office Action U.S. Appl. No. 10/004,270 mailed May 20, 2005.

Office Action U.S. Appl. No. 10/004,270 mailed Feb. 23, 2006.

Office Action U.S. Appl. No. 10/004,270 mailed Aug. 1, 2006.

Translated Japanese Office Action of Application No. 2001-564653 dated Feb. 14, 2008.

* cited by examiner

DEVICE, SYSTEM AND METHOD OF RECEIVING AND RECORDING AND DISPLAYING IN-VIVO DATA WITH USER ENTERED DATA

CROSS REFERENCE TO RELATED APPLICATIONS

This application claims the benefit of U.S. Ser. No. 60/701,986, filed on Jul. 25, 2005, which is incorporated in its entirety herein by reference.

FIELD OF THE INVENTION

The present invention relates to the field of in-vivo sensing, for example, in-vivo imaging.

BACKGROUND OF THE INVENTION

In an in-vivo sensing system, an in-vivo device, for example, an ingestible device that may move through the gastrointestinal (GI) tract, and that may collect data and transmit the data to a receiver system are known in the art. The in-vivo device, for example, a capsule of a cylindrical shape, may have a wireless telemetry system allowing transmission of desired collected data continuously or as a burst at pre-programmed time intervals via a miniature antenna via radio frequency (RF). The radio transmission is then received by, for example, a small receiver attached to the patient or in a clinic. Data from the receiver is typically transferred to a display unit for an external operator to review. The display unit may include one or more windows for showing image data and other data, typically data derived from calculations preformed by a processor in the receiver, for example, localization data, elapsed time data, and other information.

US 2004/0249291 discloses a display of an average color bar indicating the overall imaging period of images taken in time sequence by a capsule endoscope. A list of checked images in the entire taken images is displayed in a checked-image display field, computation is made to what time during an observation period each checked image corresponds is computed, and a mark is displayed with a scale of the average color bar by a number corresponding to each checked image on the average color bar.

The capsule-type medical device according to US 2003/0023150 is advanced the inside of the somatic cavities and lumens of humans being or animals for conducting examination, therapy, or treatment. The capsule-type medical device comprises a plurality of hard units and a soft linking unit which links the plurality of hard units and has a diameter less than that of any of the hard units, wherein one of the plurality of hard units is different in size from other hard units.

SUMMARY OF THE INVENTION

Some embodiments of the invention may provide, for example, an in-vivo sensing system that may be configured to receive external input (e.g., from a patient) in addition to input from an in-vivo device.

According to an embodiment of the invention, an in-vivo system may comprise, for example, an in-vivo imaging device able to transmit in-vivo data to an external receiver/recorder, and a display unit for displaying image and/or other data. The in vivo data may be transmitted, for example, via a wireless medium.

An in-vivo system according to an embodiment of the invention may further comprise a receiver that may be configured to receive in vivo data. The in vivo data may be received, for example, via a wireless medium. The in vivo data may comprise at least one of a list comprising image, time relative to the activation or insertion of the in-vivo device into a body lumen, progress of in-vivo device, localization of in-vivo device, motility of in-vivo device, pH level in said body lumen, blood presence detection in said body lumen, temperature in said body lumen and pressure in said body lumen.

An in-vivo system according to an embodiment of the invention may further comprise input means. The input means may enable the entering of indications by a user. The indications may relate to activities of said user (e.g., sleeping, eating, drinking, walking, sitting, running, or the like), conditions of said user (e.g., existence of pain with indications of its level, discomfort or the like) and/or environmental conditions of said user (temperature, humidity, or the like).

An in-vivo system according to an embodiment of the invention may further comprise an indication storage unit which may store indications entered by the user, data representing the entering time at which an indication was entered by said user and data indicating in vivo data corresponding to said entering time.

In some embodiments, the display unit may display the indications entered by the user together with in vivo data corresponding to the entering time of said indications.

In some embodiments, the display unit may be included in a work station, said work station may be adapted to do at least one of a list comprising receiving, processing, analyzing, recording, playback and displaying data. The work station may also be able to control the order and timing in which said work station receives data.

In some embodiments, indications entered by the user or data representing such indications may be displayed or presented in proximity to or in conjunction with other to data, for example, image data, time bar, color bar, progress bar, localization data, motility data, or the like.

According to an embodiment of the invention, a display unit device may display in vivo data. The display unit device may comprise, for example, a display of controls to playback the stream of images. The display unit device may comprise, for example, a time display, such as a bar indicating time. The time display may show the time related to said stream of images. The display unit device may comprise, for example, at least one graphical presentation. The graphical presentation may be associated with in vivo data. The in-vivo data may correspond to the stream of images. The display unit device may comprise, for example, an indicator. The indicator may indicate the correspondence between the graphical presentation and the stream of images with respect to time. The display unit device may comprise, for example, representations which may represent indications entered by a user. The indications may be represented in conjunction with said at least one graphical presentation of in-vivo data.

In some embodiments, for example, the display unit device may comprise controls. The controls may enable to control playback of the stream of images. An indicator may move along, for example, a time bar in correspondence with said playback to indicate the correlation of relative or absolute time to the stream of images. The indicator may also move along at least one graphical presentation of in-vivo data.

In some embodiments, the playback of the stream of images may be controllable by moving the indicator along a time bar.

BRIEF DESCRIPTION OF THE DRAWINGS

Embodiments of the invention are illustrated by way of example and not limitation in the figures of the accompanying drawings, in which like reference numerals indicate corresponding, analogous or similar elements, and in which.

Figure 1:
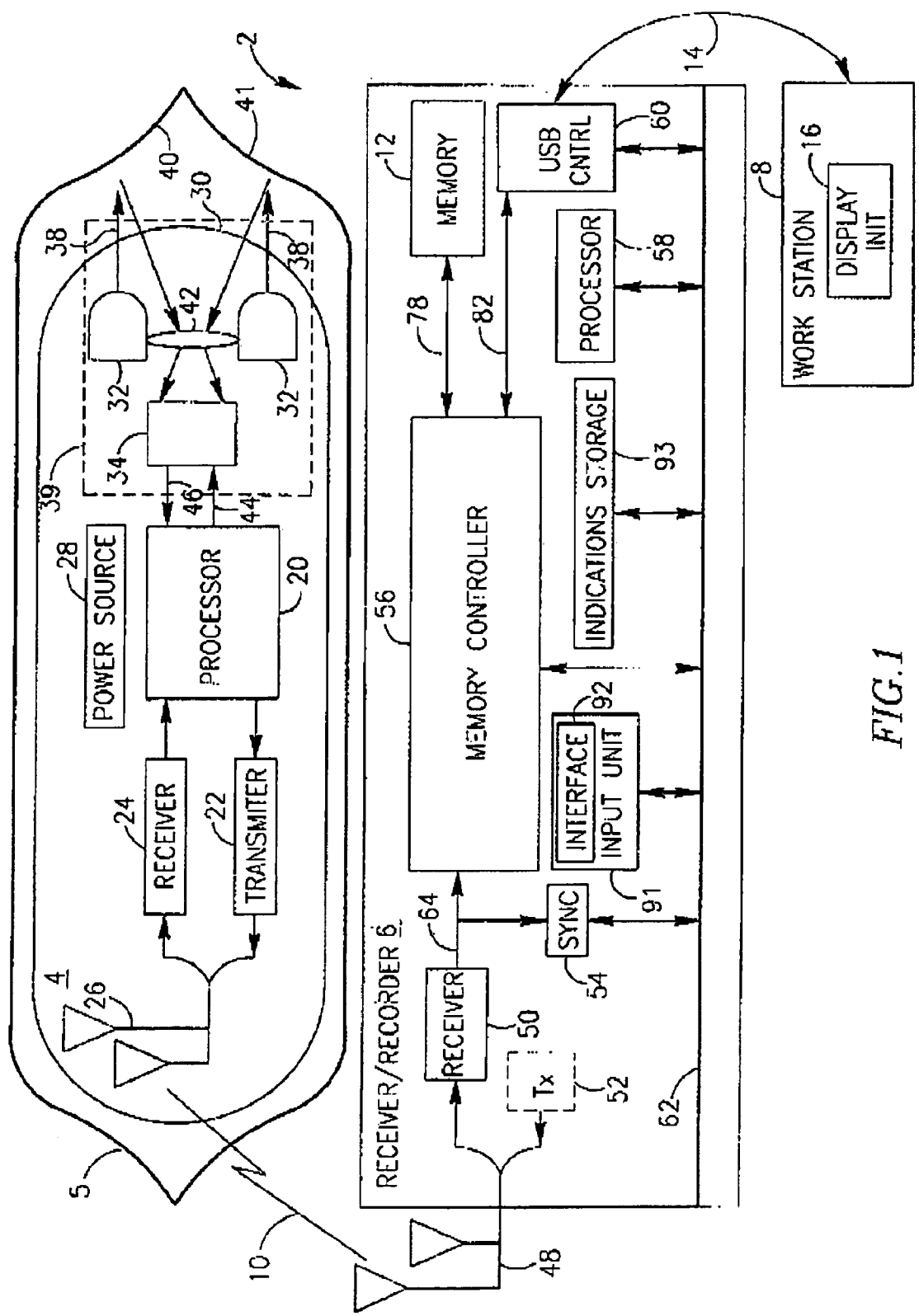
FIG. 1 is a schematic block-diagram illustration of an in-vivo sensing system in accordance with some embodiments of the invention.

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION OF THE INVENTION

In the following detailed description, numerous specific details are set forth in order to provide a thorough understanding of embodiments of the invention. However it will be understood by those of ordinary skill in the art that the embodiments of the invention may be practiced without these specific details. In other instances, well-known methods, procedures, components and circuits have not been described in detail so as not to obscure the embodiments of the invention.

Although a portion of the discussion may relate to in-vivo imaging devices, systems, and methods, the present invention is not limited in this regard, and some embodiments of the present invention may be used in conjunction with various other in-vivo sensing devices, systems, and methods. For example, some embodiments of the invention may be used, for example, in conjunction with in-vivo sensing of pH, in-vivo sensing of temperature, in-vivo sensing of pressure, in-vivo sensing of electrical impedance, in-vivo detection of a substance or a material, in-vivo detection of a medical condition or a pathology, in-vivo acquisition or analysis of data, and/or various other in-vivo sensing devices, systems, and methods.

Some embodiments of the present invention are directed to a typically swallowable in-vivo sensing device, e.g., a typically swallowable in-vivo imaging device. Devices, systems, and methods of the present invention may be used with, or in, an imaging system such as that described in U.S. Pat. No. 7,009,634 to Iddan et al, entitled "Device for In-Vivo Imaging", issued on Mar. 7, 2006. A further example of an imaging system, with which or in which devices, systems and methods of the present invention may be used, is described in U.S. Pat. No. 5,604,531 to Iddan et al., entitled "In-Vivo Video Camera System", issued on Feb. 18, 1997. Both these publications are assigned to the common assignee of the present application and are incorporated herein by reference in their entirety. The device, system and method of the present invention may be utilized in conjunction with other suitable imaging or sensing devices, systems and methods. Devices and systems as described herein may have other configurations and/or other sets of components. For example, some embodiments of the present invention may be practiced using an endoscope, a probe, a needle, a stent, a catheter, etc.

Some embodiments of the present invention may be or may include an autonomous swallowable capsule, but may have other shapes and need not be swallowable or autonomous. Embodiments are typically self-contained, but need not be. For example, a device according to some embodiments may be a capsule or other unit where all the components are substantially contained within a container or shell, and where the device does not require any wires or cables to, for example, receive power or transmit information.

Devices and systems described herein may have other suitable configurations and other sets of components, and may be used in conjunction with other devices, non-imaging devices and/or non-in-vivo devices.

Some embodiments of the present invention are directed to a typically swallowable device that may passively or actively progress through the gastro-intestinal (GI) tract, pushed along, in one example, by natural peristalsis. Other embodiments are directed at in-vivo sensing devices that may be passed through other body lumens such as through blood vessels, the reproductive tract, etc. The device may be a sensing device, an imager, a diagnostic device, a therapeutic device, or a combination thereof. Devices as described herein may have other configurations and sets of components.

FIG. 1 is a schematic illustration of an in-vivo sensing system 2, including an in-vivo sensing device 4, such as an in-vivo imaging device, a receiver/recorder 6 and a workstation 8, in accordance with some embodiments of the invention. According to some embodiments, sensing device 4 may be, for example, an oblong, oval, or spherical, and may be swallowable, although other configurations are possible and are within the scope of the invention.

Sensing device 4, contained in a housing wall 5, may be able to gather information in-vivo, such as, for example, a stream of images of inner walls of body lumens while passing through inside of a patient's body, and may be able to transmit at least that information to receiver/recorder 6 outside the patient's body via a wireless or hard-wired medium 10. Sensing device 4 may include, for example, an imaging system 39, a processor 20, a transmitter 22, an optional receiver 24, and at least one antenna 26. In addition, sensing device 4 may include a power source 28 (e.g., one or more batteries or power cells) to provide power to at least imaging system 39, processor 20, transmitter 22, and optional receiver 24. Sensing device 4 may include an optical window 30, at least one illumination source 32, such as, for example, a Light Emitting Diode (LED), an imaging sensor 34, and an optical system 36.

Illumination source 32 may produce light rays 38 that may penetrate through optical window 30 and may illuminate an inner portion 40 of a body lumen 41. A non-exhaustive list of examples of body lumen 41 includes the gastrointestinal (GI) tract, a blood vessel, the reproductive tract, or any other suitable body lumen.

Reflections 42 of light rays 38 from inner portion 40 of body lumen 41 may penetrate optical window 30 back into sensing device 4, and may be focused or directed by optical system 36 onto imaging sensor 34. Imaging sensor 34 may receive the focused reflections 42, and in response to an image capturing command 44 from processor 20, imaging sensor 34 may capture an image of inner portion 40 of body lumen 41. Processor 20 may receive the image of inner portion 40 from imaging sensor 34 over wires 46, and may control transmitter 22 to transmit the image of inner portion 40 through antenna 26 into wireless medium 10. Sensing device 4 may passively or actively progress along an axis of body lumen 41. In time intervals that may or may not be substantially equal and may or may not be related to that progress, processor 20 may initiate capturing of an image by imaging sensor 34, and may control transmitter 22 to transmit the captured image. Consequently, a stream of images of inner portions of body lumen 41 may be transmitted from sensing device 4 into wireless medium 10.

Receiver/recorder 6 may include a memory 12, and may be able to record information received from sensing device 4 on memory 12. Optionally, receiver/recorder 6 may include a display panel 18 which may include an LCD, TFT, CRT, OLED or other suitable panels. The display panel 18 may be integrated into to receiver/recorder 6. Receiver/recorder 6 may be able to transfer the received and/or recorded information to display 18 or to workstation 8 via, for example, a wireless or hard-wired medium 14, and may be able to do so while receiving/recording information from sensing device 4.

Workstation 8 may be able to process and/or present information received from receiver/recorder 6 to an operator while sensing device 4 is still inside the patient's body, and while receiver/recorder 6 is still recording information gathered by sensing device 4. For example, workstation 8 may include a display unit 16, and may be able to display the stream of images recorded in memory 12 on display unit 16. Display unit 16 may include an LCD, TFT, CRT, OLED or other suitable medium.

By sending control signals to receiver/recorder 6 via, for example, wireless or hard-wired medium 14, workstation 8 may be able to control the way in which receiver/recorder 6 transfers recorded information to workstation 8. In view of such controls, in the example of a stream of images, receiver/recorder 6 may perform any of the following exemplary operations, although this is a non-exhaustive list: start or stop sending images to workstation 8, send the stream of images in the order received from sensing device 4 or in reverse order, start sending images to workstation 8 from a specific image in the stream, defined by, for example, a human operator of workstation 8, and the like.

Memory 12 may be fixed in or removable from receiver/recorder 6. A non-exhaustive list of examples of memory 12 includes any combination of the following semiconductor devices such as registers, latches, electrically erasable programmable read only memory devices (EEPROM), not AND (NAND) flash memory devices, not OR (NOR) flash memory devices, non-volatile random access memory devices (NVRAM), synchronous dynamic random access memory (SDRAM) devices, RAMBUS dynamic random access memory (RDRAM) devices, double data rate (DDR) memory devices, static random access memory (SRAM), universal serial bus (USB) removable memory, compact flash (CF) memory cards, personal computer memory card international association (PCMCIA) memory cards, security identity module (SIM) cards, MEMORY STICK cards, and the link; optical devices, such as compact disk read-only memory (CD ROM), compact disk recordable memory (CD-R), and the like; and magnetic devices, such as a hard disk, a floppy disk, a magnetic tape, and the like.

A non-exhaustive list of examples of imaging sensor 24 includes a solid state imaging sensor, a Complementary Metal Oxide Semiconductor (CMOS) imaging sensor, a Charge Coupled Device (CCD) imaging sensor, a linear imaging sensor, a line imaging sensor, a full frame imaging sensor, a "camera on chip" imaging sensor, or any other suitable imaging sensor.

A non-exhaustive list of examples of power source 28 includes batteries, such as, for example, silver oxide batteries, lithium batteries, capacitors, or any other suitable power source. In another embodiment of the present invention, power source 28 may not be present and the device may be powered by an external power source.

Receiver/recorder 6 may include at least one antenna 48, a receiver 50, an optional transmitter (TX) 52, a payload/frame synchronizer 54, a memory controller 56, a processor 58, and a communication controller, such as, for example, a Universal Serial Bus (USB) controller 60.

Processor 58 may be able to control the operation of receiver 50, optional transmitter 52, payload/frame synchronizer 54, memory controller 56, and USB controller 60 through a bus 62. In addition, receiver 50, optional transmitter 52, payload/frame synchronizer 54, memory controller 56, processor 58 and USB controller 60 may be able to exchange data, such as, for example, images received from sensing device 4, or portions thereof, over bus 62.

Antenna(s) 48 may be mounted inside or outside receiver/recorder 6 and both receiver 50 and optional transmitter 52 may be coupled to antenna 48. Optional transmitter 52 may be able to transmit wireless messages to sensing device 4 through antenna 48. Receiver 50 may be able to receive transmissions, such as, for example, a stream of wireless communication frames, from sensing device 4 through antenna 48, and may output bits corresponding to the wireless communication frames on traces 64.

Receiver/recorder 6 may communicate with workstation 8 via hard-wired medium 14. For example, receiver/recorder 6 may be able to transfer recorded payloads to work station 8, and may be able to receive controls from workstation 8. Although the invention is not limited in this respect, hard-wired medium 14 may be, for example, a USB cable and may be coupled to USB controller 60 of receiver/recorder 6 and to workstation 8.

A non-exhaustive list of examples of antennae 26 and 48 includes dipole antennae, monopole antennae, multilayer ceramic antennae, Planar inverted-F antennae, loop antennae, shot antennae, dual antennae, omni-directional antennae, coil antennae or any other suitable antennas. Moreover, antenna 26 and antenna 48 may be of different types.

A non-exhaustive list of examples of processors 20 and 58 may include a central processing unit (CPU), a digital signal processor (DSP), a reduced instruction set computer (RISC), a complex instruction set computer (CISC) and the like. Moreover, processors 20 and/or 58 may each be part of an application specific integrated circuit (ASIC) or may each be a part of an application specific standard product (ASSP).

A non-exhaustive list of examples of work station 8 includes a original equipment manufacturer (OEM) dedicated work station, a desktop personal computer, a server computer, a laptop computer, a notebook computer, a handheld computer, and the like.

In some embodiments, receiver/recorder 6 may optionally include an input unit 91, for example, a unit or sub-unit able to receive input or data entered (e.g., manually) by a user. For example, a patient may use the input unit 91 to enter indications or signals related to the patient's activity or conditions to the receiver/recorder 6. In some embodiments, for example, the input unit 91 may include a user interface 92 to allow the user to enter such indications. The user interface 92 may include, for example, one or more buttons, press-able buttons, touch-buttons, switches, sliders, keypad, keyboard, or the like.

In one embodiment, for example, the user interface 92 may include multiple buttons allowing the user to enter indications or "marks" of one or more activities or conditions, respectively. For example, interface 92 may include a button which may be pressed by a user to indicate that the user is eating, or has finished eating, a button which may be pressed by a user to indicate that the user is drinking or has finished drinking, a button which may be pressed by a user to indicate that the user is feeling general pain or discomfort, a button which may be pressed by a user to indicate that the user is feeling specific pain or discomfort (e.g., stomach pain), a button which may be pressed by a user to indicate that the user is feeling gases, a button which may be pressed by a user to indicate that the user is feeling sick, a button which may be pressed by a user to indicate that the user is performing (starts to perform, or finishes to perform) a certain activity (e.g., sleeping, sitting, running, walking, or the like), and other suitable buttons. In some embodiments, multiple buttons may correspond to multiple degrees or severity of a certain condition, for example, a first button may be used to indicate severe pain, a third button may be used to indicate light pain, or the like.

In another embodiment, for example, the input unit 91 and/or the interface 92 may allow the user to enter numbers or text indications of one or more activities or conditions. For example, the input unit 91 and/or the interface 92 may allow the user to enter a pre-defined code to indicate a certain condition or activity, to type or enter "free text" describing a certain condition or activity, to select a condition or activity from a list or menu presented to the user (e.g., through an optional screen included in the input unit 91 and/or the interface 92), or the like.

In some embodiments, an indication entered through the input unit 91 and/or the interface 92, may be recorded and stored, for example, in an indication storage unit 93. In some embodiments, the indication storage unit 93 may be a separate sub-unit of receiver/recorded 6, or may be implemented as part of, for example, memory 12 or other sub-unit of receiver/recorder 6. The indication storage unit 93 may store, for example, data representing the indication entered by the user, data representing the time at which the indication was entered by the user, data representing the sequential number or other property of the image or frame acquired or stored immediately before or immediately after the indication was entered, or the like.

In some embodiments, the input unit 91 and/or the indication storage unit 93 may be operatively connected to the bus 62, to allow transfer and/or sharing of data entered through the input unit 91 and/or stored in the indication storage unit 93. In one embodiment, the input unit 91 may optionally be directly connected to the indication storage unit 93. Other suitable configurations or connections may be used.

In some embodiments, one or more indications stored in the indication storage unit 93 may be displayed, presented, processed and/or analyzed. In one embodiment, for example, a list of substantially all indications, and the times at which the indications were entered by the users, may be generated and presented to a user (e.g., through workstation 8, display unit 16, or a printer or other output unit operatively connected to the workstation 8). In another embodiment, the indications may be presented as a function of time, e.g., in the form of a plotted graph.

In some embodiments, indications stored in the indication storage unit 93 may be displayed on display unit 16 together (e.g., substantially simultaneously) with other data acquired by the in-vivo device and/or recorded by the receiver/recorder 6, for example, image data, location data, position data, motility data, pH data, temperature data, pressure data or the like. In some embodiments, for example, the display unit 16 may present images acquired by the in-vivo device (image data), data indicating a sequential number of the image or frame currently displayed (frame number), data indicating absolute time or relative time (e.g., relative to the activation or insertion of the in-vivo device), data presented using bars or graphs (e.g., motility bar, tissue bar, time bar, or the like), and/or data representing one or more indications entered through the input unit 91 and/or stored in the indications storage unit 93.

Figure 2:
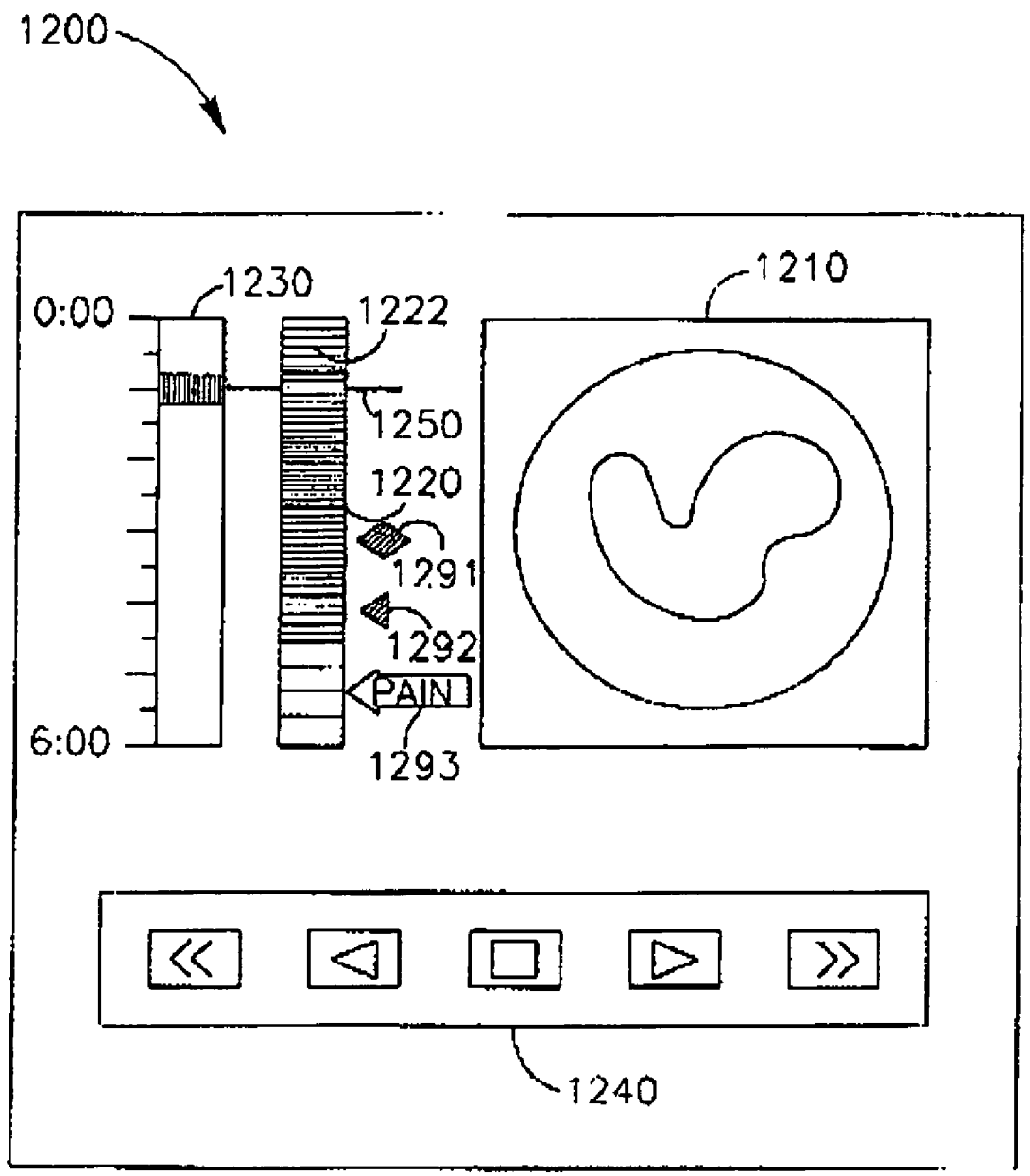
FIG. 2 is a schematic illustration of a display of a color bar together with other data captured in-vivo and with user input in accordance with an embodiment of the invention.

Reference is now made to FIG. 2 showing a display and/or a graphical user interface 1200 for displaying data captured in-vivo data. Display 1200 may include a summarized graphical presentation 1220 of an in-vivo data stream, for example, a color bar. Typically, the graphical presentation 1220 may be a fixed presentation displayed alongside a streaming display of a data stream 1210, for example, an image stream in accordance with some embodiments of the present invention. In other embodiments, graphical presentation 1220 may be displayed separately.

In some embodiments, the graphical presentation 1220 may include, for example, a series of colors, a series of colored areas, or a series of patterns, image items, images or pixel groups (e.g., a series of stripes 1222 or areas of color arranged to form a larger bar or rectangular area), where each, for example, color in the series 1222 may be associated with and/or correspond to an element or a group of elements in the original data stream. For example, each colored stripe 1222 may correspond to an image or a group of images from a data stream 1210. Image units other than stripes (e.g., pixels, blocks, etc.) may be used, and the image units may vary in a dimension other than color (e.g., pattern, size, width, brightness, animation, etc). One image unit (e.g., a stripe 1222) may represent one or more units (e.g., image frames) in the original data stream. Typically, the series of, for example, colors in the bar may be arranged in the same sequence or order in which the data stream, for example, the images or groups of images may typically be displayed. In one embodiment, pointing at a stripe in a graphical presentation 1220 may advance the image stream to the frames corresponding to that stripe.

In one embodiment, a stream of data 1210 may be displayed along one or more bars and/or graphical presentations (1220 and 1230) described herein. The data stream 1210 may be for example data represented in the graphical presentation 1220 (e.g. a captured in-vivo image stream) or other data obtained and/or sampled simultaneously or substantially simultaneously with the data represented in the graphical presentation 1220. In one example, a marker or indicator 1250 may progress across or along the graphical presentation 1220 as the substantially corresponding datum in data stream 1210 (e.g., video) may be concurrently displayed to indicate the correspondence between the graphical presentation 1220 and the data stream 1210. In other embodiments, the presentation may be of a shape other than a bar, for example a circle, oval, square, etc. According to other embodiments, the presentation may be in the form of an audio tract, graph, and other suitable graphic presentations.

An indicator 1250 such as a cursor may advance along the time bar 1230 and graphical presentation 1220 as the image stream 1210 is playbacked on the display 1200. In one example, control buttons 1240 may be included in the display that may allow the user to, for example, fast-forward, rewind, stop play or reach the beginning or end of, for example, an image stream 1210. In other embodiments, a user may control the display of a data stream 1210, for example, by altering the start position of the streaming display, e.g. skipping to areas of interest, by moving the position of indicator 1250, for example with a mouse or other pointing device.

In some embodiments, a user and/or health professional may insert indications or markers such as thumbnails to mark location along the image stream for easy access to those locations in the future. For example, a health professional may mark these milestones on the graphical presentation 1220 (e.g., using a pointing device such as a mouse, a keyboard, etc).

In some embodiments, one or more indications or labels (e.g., labels 1291, 1292 and 1293) may be presented in proximity to or in conjunction with color bar 1220, time bar 1230, or other graphical representations displayed (e.g., on the display unit). In one embodiment, the indications or labels 1291-1293 may include indications stored in the indications storage unit 93 of FIG. 1, and/or entered through the input unit 91 of FIG. 1. For example, a first type (e.g., color or shape) of label 1291 may represent a first indication entered by the patient, and a second type (e.g., color or to shape) of label 1292 may represent a second, different indication entered by the patient. In one embodiment, label may include textual representation or codes, for example, as shown in label 1293. Other types of labels, indications or representations may be used.

In some embodiments, labels or indications may be displayed at a position corresponding to a relevant portion in the time bar 1230 and/or the color bar 1220. For example, a user may enter an indication of pain at a certain time, using the input unit 91 of FIG. 1, the indication may be recorded and stored in the indications storage unit 93 of FIG. 1, and may be presented in proximity to the portion of the time bar 1230 corresponding to the time in which the indication was entered, in proximity to the portion of the color bar 1220 corresponding to the relative location or progress of the in-vivo device. Other suitable configurations may be used to display indications entered by the patient.

Figure 3:
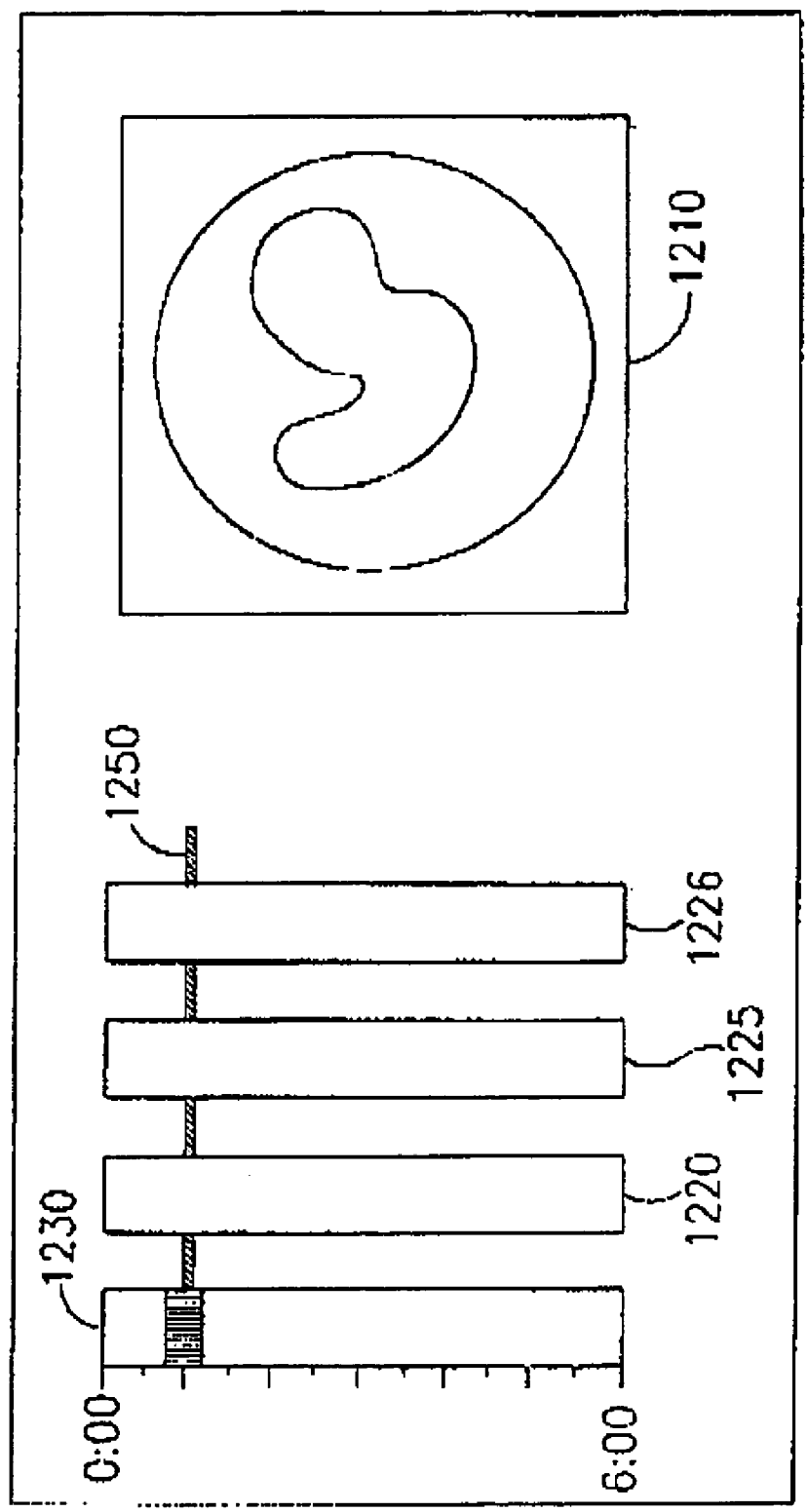
FIG. 3 is a display with more than one color bar that may be viewed substantially simultaneously according to an embodiment of the invention.

Reference is now made to FIG. 3 showing schematically a graphical user interface for viewing a streaming display of in-vivo data 1210 along with multiple fixed summarized graphical presentations 1220, 1225, and 1226 of a data stream. A single indicator 1250 may be used along with a time bar 1230 to point to a position along the fixed presentation of the data streams (1220, 1225, and 1226) so as to indicate where along the bars the data 1210 presently being displayed originated. The individual color bars may include for example, a tissue graphical presentation 1220, a pH color bar 1225, and a blood detector color bar 1226. Other number of graphical presentations, other suitable types of bars summarizing other data, and other suitable types of presentations may be used. Multiple graphical presentations may be helpful in diagnosis of medical conditions as well as locating within a stream of data, sites of interest. Multiple graphical presentation and user indications, according to embodiments of the invention, may increase the parameters that are available to a health professional when reviewing, for example, an image stream and may give a better indication of the environmental condition that may exist at a point of observation of the in-vivo sensing device 4. For example, in one embodiment, pH level, temperature and tissue graphical presentations or other presentation may be displayed, possibly, side by side.

A physician may choose which parameters he/she is interested in viewing as a map or summary. Having more than one set of parameter available at one time may make it easier to find more anatomical sites and to identify areas that may, for example, contain pathologies. According to some embodiments of the invention, information introduced by the patient in combination with in-vivo information transmitted from the in-vivo device may facilitate the physician's diagnosis. Numerous algorithms based on case studies or other suitable data may be applied to suggest to the physician alert sites or other information obtained from one or more color bars or from the combination of one or more color bars and in combination with user input. Other suitable indicating maps, information summaries, or color bars may be used.

Figure 4:
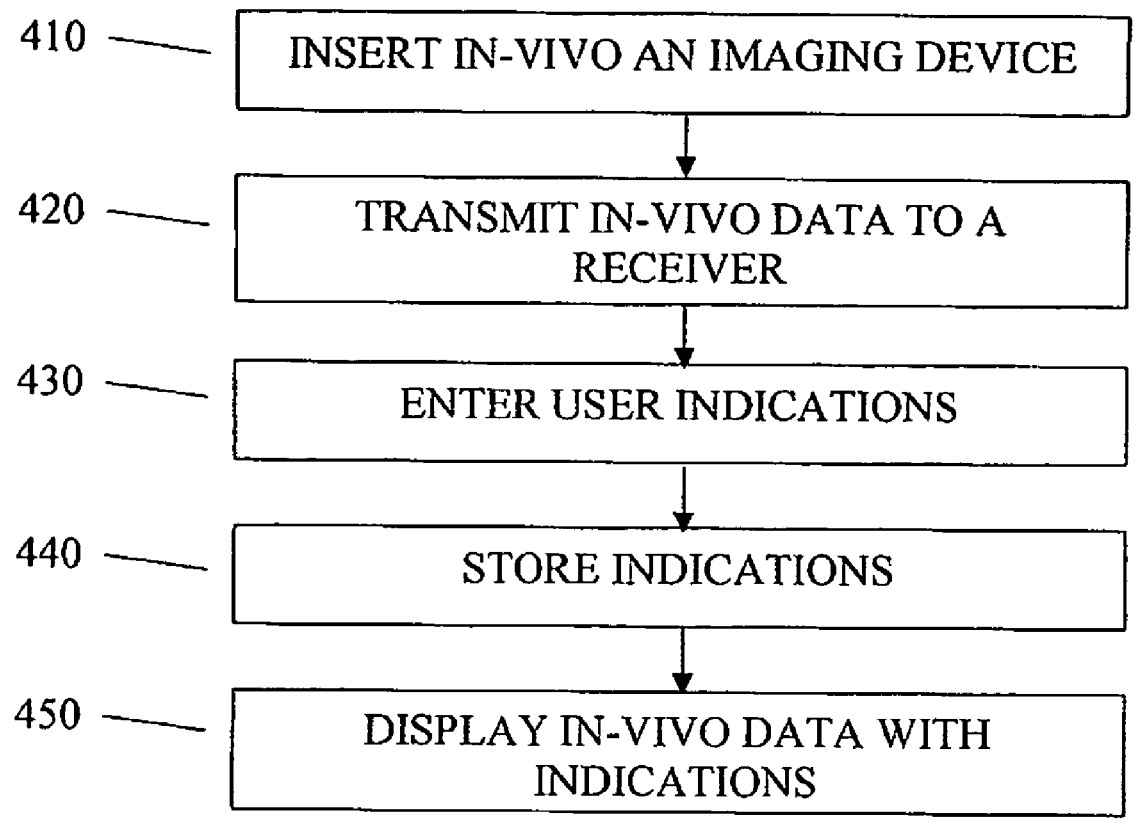
FIG. 4 is a flowchart depicting a method according to an embodiment of the invention.

Reference is now made to FIG. 4, which depicts a method for adding user indications to an in-vivo image display according to embodiments of the invention. According to one embodiment, a patient may insert an imaging device or imaging capsule (e.g., as described above) in-vivo (box 410). The imaging capsule or imaging device may transmit data obtained from within the patient's body (e.g., from the patient's GI tract or from other body lumens) to an external receiver/recorder system (e.g., as described above) (box 420). Typically data, e.g., image data, may be transmitted continuously or substantially continuously from the imaging capsule or imaging device, and may be received and optionally recorded by the receiver/recorder. The received data may then be downloaded or transferred from the receiver/recorder to a display unit, for example, a monitor or workstation, a Personal Computer, a portable computer screen, a laptop, or the like.

In some embodiments, the patient may press a button or use another input means or interface for entering to the receiver/recorder unit one or more user indications (box 430). For example, the patient may indicate his own activities, sensations, or other parameters or events. A single button or several different buttons or means may be used to input a user indication. The patient input may be stored (box 440), and may be incorporated and shown together with in-vivo data (box 450), for example with a display of endo-luminal images. Other ways of displaying the patient input may be used, for example, a map or summary of the patient indications, shown alone or together with in-vivo information, e.g., motility, location, position, orientation, temperature, pressure, pH values, images, other sensed parameters, or the like.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the spirit of the invention.

What is claimed is:

1. A method comprising the steps of:
  acquiring frames of in vivo image data by a capsule endoscope during the passage of said capsule endoscope through a body lumen of a patient;
  transmitting by said capsule endoscope said in vivo image data from within said body lumen to a receiver outside the patient's body;
  storing in the receiver said frames of in vivo image data;
  receiving at the receiver at least one indication by said patient during the passage of said capsule endoscope through a body lumen of said patient, wherein said indication is selected from: activities of said patient, condition of said patient, and environment of said patient;
  storing in the receiver said at least one indication together with data representing a property of at least one frame of said frames of in vivo image data acquired immediately before or immediately after said at least one indication was received;
  transferring said stored frames of in vivo image data, said at least one indication, and said data representing the property of the at least one frame from said receiver to a workstation; and
  displaying simultaneously by said workstation a stream of said frames of in vivo image data, a time bar, a summarized graphical representation of said stream of said frames of in vivo image data, and a representation of said at least one indication, wherein said representation of said at least one indication is displayed at a position relative to said time bar and said fixed summarized graphical representation corresponding to the time in which said at least one indication was received at said receiver.

2. The method according to claim 1, further comprising the step of controlling playback of said stream of frames of in vivo image data.

3. The method according to claim 1, further comprising storing in the receiver said indication, data representing the entering time at which said indication was entered by said patient, and data identifying a portion of said in vivo image data which corresponds to said entering time.

4. The method according to claim 1, wherein said displaying comprises displaying a graphical presentation associated with in-vivo data in time-correlation with said displayed stream of frames of in vivo image data.

* * * * *